(12) United States Patent
Leonard

(10) Patent No.: US 7,397,041 B1
(45) Date of Patent: Jul. 8, 2008

(54) APPARATUS FOR SANITIZING OBJECTS

(76) Inventor: Michael C. Leonard, 6 Orchard St., Branchville, NJ (US) 07826

( * ) Notice: Subject to any disclaimer, the term of this patent is extended or adjusted under 35 U.S.C. 154(b) by 324 days.

(21) Appl. No.: 11/388,952

(22) Filed: Mar. 27, 2006

(51) Int. Cl.
*G01N 23/00* (2006.01)

(52) U.S. Cl. .............................. 250/455.11; 250/453.11; 250/454.11

(58) Field of Classification Search ................................. 250/453.11–455.11
See application file for complete search history.

(56) References Cited

U.S. PATENT DOCUMENTS

| | | | | |
|---|---|---|---|---|
| 4,088,445 A | * | 5/1978 | Ellis | ............................ 312/207 |
| 4,309,388 A | * | 1/1982 | Tenney et al. | ................ 422/304 |
| 4,449,050 A | | 5/1984 | Kamhi | |
| 2007/0138407 A1 | * | 6/2007 | Mcinnes et al. | ......... 250/453.11 |

* cited by examiner

*Primary Examiner*—Jack I. Berman
*Assistant Examiner*—Andrew Smyth
(74) *Attorney, Agent, or Firm*—Donald A. Kettlestrings

(57) ABSTRACT

Apparatus for sanitizing objects by use of ultraviolet light includes an enclosed container defining a first object entry opening and a second object exit opening. A first inclined slide is mounted within the container and is positioned adjacent to the first entry opening, and a second inclined slide is mounted within the container beneath the first slide and positioned adjacent to the second exit opening. The slides are positioned at angles with respect to horizontal such that the pull of gravity on the objects moving down each of the slides is greater than restraining electrostatic or frictional forces on the objects. A baffle is mounted within the container and is positioned with respect to the slides for redirecting objects from the first slide onto the second slide, and ultraviolet light sources are mounted in the container and positioned above the slides for irradiating the objects as they move down the slides.

10 Claims, 2 Drawing Sheets

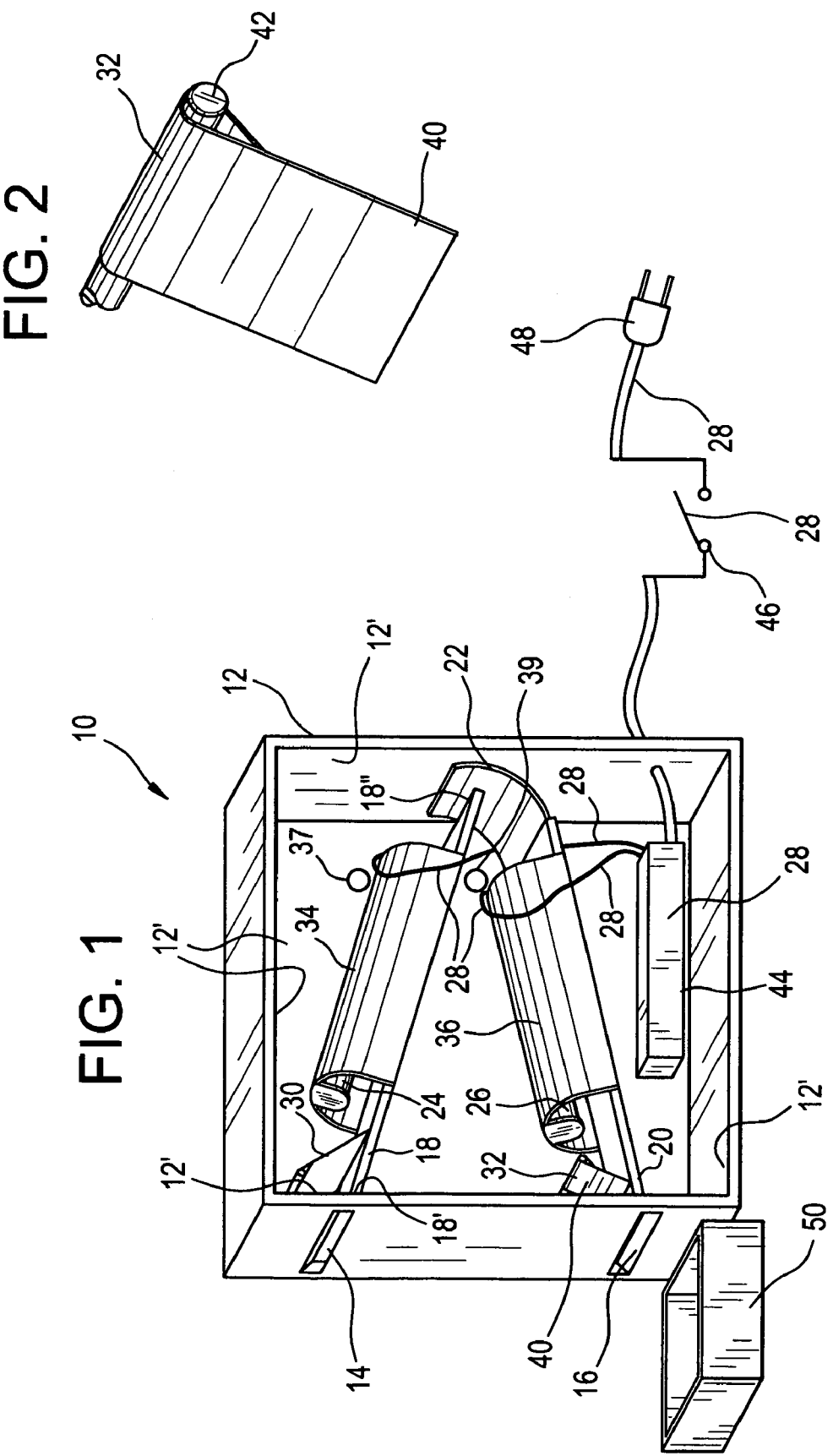

APPARATUS FOR SANITIZING OBJECTS

BACKGROUND OF THE INVENTION

This invention relates to apparatus for sanitizing objects and more particularly to apparatus for sanitizing objects by use of ultraviolet light.

The use of ultraviolet lamps, and specifically UVC germicidal light tubes or lamps, for sanitizing objects is well known. However, existing ultraviolet sanitizing devices have not provided a compact size without complex moving parts for quickly and thoroughly sanitizing all sides of objects.

Studies have shown that bacteria can live for up to twenty-four hours on surfaces, such as hotel keys, credit cards, identification cards used by hospital personnel and others, coins, poker chips, playing cards, hair combs, etc.

It is, therefore, an object of the present invention to provide apparatus for sanitizing objects by use of ultraviolet light.

Another object is to provide such apparatus which is compact in size for convenient placement adjacent to cash registers, hotel desks, nursing stations or other easily accessible locations.

A further object of the invention is the provision of such apparatus which does not require expensive and complex moving parts for its operation.

Yet another object of the present invention is the provision of such apparatus which can sanitize objects of various sizes and shapes.

A still further object is to provide such apparatus which can be used by hotel or hospital personnel or by the general public to quickly and easily sanitize objects.

Another object is to provide such apparatus which effectively sanitizes all sides of the objects.

Still another object is to provide such apparatus which effectively sterilizes objects of bacteria, viruses and yeasts.

Additional objects and advantages of the invention will be set forth in part in the description which follows, and in part will be obvious from the description, or may be learned by practice of the invention. The objects and advantages are realized and attained by means of the instrumentalities and combinations particularly pointed out in the appended claims.

BRIEF SUMMARY OF THE INVENTION

To achieve these and other objects, the present invention provides apparatus for sanitizing objects by use of ultraviolet light, comprising: an enclosed container defining a first object entry opening of predetermined height and a second object exit opening of at least said predetermined height; a first inclined slide mounted within the container positioned adjacent to the first entry opening; a second inclined slide mounted within the container beneath the first slide and positioned adjacent to the second exit opening; the first and second inclined slides positioned at angles with respect to horizontal such that the pull of gravity on the objects moving down each of the slides is greater than restraining electrostatic or frictional forces on the objects; a baffle mounted within the container and positioned with respect to the first and second slides for redirecting objects from the first slide onto the second slide; a first ultraviolet light source mounted within the container and positioned above the first slide; a second ultraviolet light source mounted within the container and positioned above the second slide; and means in operative relationship with the first and second light sources for selectively operating the light sources.

BRIEF DESCRIPTION OF THE SEVERAL VIEWS OF THE DRAWINGS

The accompanying drawings, which are incorporated in and constitute a part of this specification, illustrate a preferred embodiment of the invention and, together with the description, serve to explain the principles of the invention.

FIG. 1 is a diagrammatic perspective illustration of the sanitizing apparatus;

FIG. 2 is a fragmentary perspective view showing one of the ultraviolet lights shielding members.

DETAILED DESCRIPTION OF THE INVENTION

Figure 3:
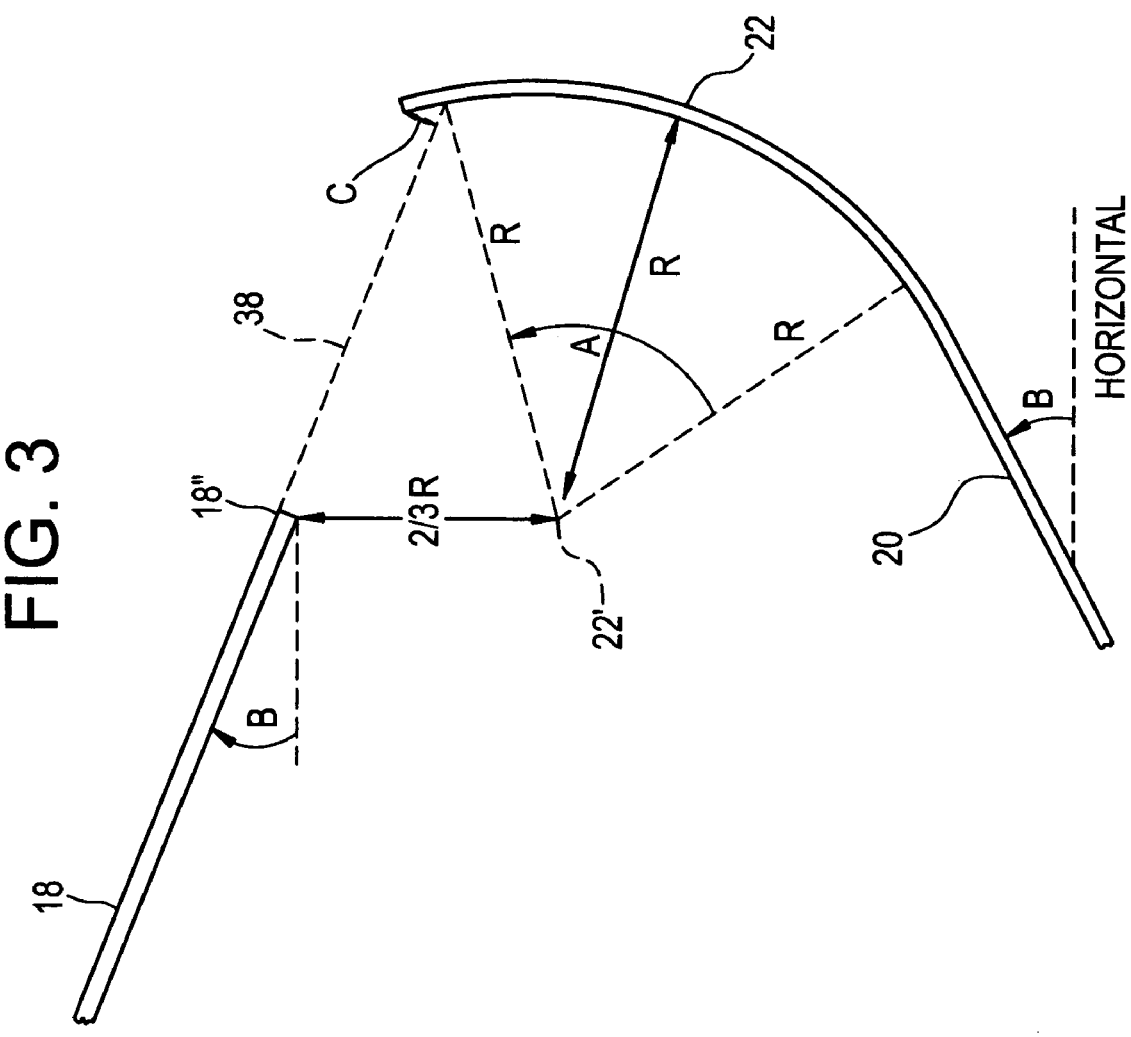
FIG. 3 is a fragmentary diagrammatic view showing the geometric relationships between the first and second slides and the baffle.

With reference now to the drawings, wherein like reference characters designate like or corresponding parts throughout the several views, there is shown apparatus 10 in accordance with the invention for sanitizing objects by use of ultraviolet light.

Apparatus 10 includes an enclosed container 12 defining a first object entry opening or slot 14 of predetermined height and width and a second object exit opening or slot 16 of at least the height and width of first opening 14.

A first inclined slide 18 is conventionally mounted within container 12 and is positioned adjacent to and below first entry opening 14. A second inclined slide 20 is conventionally mounted within container 12 beneath first slide 18 and is positioned with an end of slide 20 adjacent to and below second exit opening 16.

Slides 18, 20 are positioned within container 12 at angles with respect to horizontal such that the pull of gravity on objects moving down each of the slides is greater than restraining electrostatic or frictional forces on the objects.

A baffle 22 is conventionally mounted within container 12 and is positioned with respect to slides 18, 20 for flipping and redirecting objects from first slide 18 onto second slide 20.

A first ultraviolet light source, such as a UVC lamp or tube, 24 is conventionally mounted within container 12 and is positioned above first slide 18. A second ultraviolet light source, such as a UVC lamp or tube, 26 is conventionally mounted with container 12 and is positioned above second slide 20.

Means 28 are conventionally provided in operative relationship with light sources 24, 26 for selectively operating the light sources.

A first ultraviolet light shielding member 30 is yieldingly mounted within container 12 adjacent to first entry opening 14 and adjacent to first slide 18 for enabling the objects to be sanitized to move past shielding member 30 as the objects pass through opening 14 and move downwardly on first slide 18. Similarly, a second ultraviolet light shielding member 32 is yieldingly mounted within container 12 adjacent to second exit opening 16 and adjacent to second slide 20 for enabling the objects to be sanitized to move past shielding member 32 as the objects move downwardly on second slide 20 and outwardly through exit opening 16.

A first ultraviolet light reflector 34 is conventionally mounted within container 12 above first slide 18 and partially around first ultraviolet light source 24. A second ultraviolet light reflector 36 is similarly conventionally mounted within container 12 above second slide 20 and partially around second light source 26.

Each of reflectors 34, 36 preferably defines a parabolic shape and is positioned with light sources 24, 26 at the focus of reflectors 34, 36, respectively.

Container 12 further defines first and second ultraviolet light filtered openings 37, 39 positioned adjacent to light sources 24, 26, respectively, for enabling visual verification that light sources 24, 26 are operating properly without damage to the observer's eyes from the ultraviolet light.

Baffle 22 defines a circular arc. First slide 18 defines a first end 18' positioned adjacent to and below first entry opening 14 and a second end 18" positioned adjacent to baffle 22. Baffle 22 defines a radius of R, see FIG. 3, with the center of radius R or the center of the arc of baffle 22 positioned directly below second end 18" at a distance of ⅔R from second end 18". The arc of baffle 22 subtends an angle A equal to −2.33B plus 134 where B is the angle of first slide 18 with respect to horizontal. The arc of baffle 22 further extends upwardly beyond an imaginary extension line 38 from first slide 18 by a perpendicular distance C from line 28 at least equal to the height of first opening 14.

Baffle 22 is tangentially connected to second slide 20 so as to form a continuous surface from baffle 22 to slide 20 for enabling the objects being sanitized to move smoothly from baffle 22 onto second slide 20.

Container 12 also defines interior surfaces 12' which are each preferably covered with material for reflecting ultraviolet light from light sources 24, 26. This provides for all surfaces of the objects to be exposed to the ultraviolet light so that all object surfaces are sanitized.

Shielding members 30, 32 are similarly configured with respect to each other, and shielding member 32 is shown in FIG. 2. Shielding member 32 includes a free-hanging tab 40 mounted on peg 42. Peg 42 is, in turn, conventionally mounted within container 12. Tab 40 is freely rotatable about peg 42, and tab 40 is normally resting on slide 20 to block passage of ultraviolet light from light source 26 through second opening 16.

Tab 40 is made from a very thin and lightweight material, such as paper, thin sheet metal, plastic or the like. Because tab 40 is light in weight, it does not interfere with movement of an object to be sanitized past and under tab 40.

The configurations of shielding members 30, 32 with free-hanging tabs 40 allow for openings 14, 16 to be varied in height in the manufacture of apparatus 10 to accommodate a variety of objects of different heights or thicknesses, such as poker chips, combs, etc. to be sanitized by apparatus 10.

The width of container 12, openings 14, 16 and slides 18, 20 is determined by the width of objects to be sanitized. For example, the width could be 2¼ inches to accommodate credit cards, but the width could be greater to accommodate larger objects, such as ID cards or playing cards. Of course, the width could also be made smaller to accommodate smaller objects.

Light sources or lamps 24, 26 can be of various lengths and wattages. For example, an 8 inch 8 W lamp, rated at 5378 uW per sq. cm at 6 inches from the lamp, is available. In one embodiment of apparatus 10, credit cards pass 0.75 inch from the lamp (8 times the radiation at 6 inches). With 8 inch lamps, cards would be under each lamp for about 0.5 seconds, giving a dose of 21512 uW per sq. cm. This will provide over 90% kill rate for all but anthrax spores and a 100% kill rate for most bacteria and viruses. Reflective surfaces 12' in container 12 increase the kill rate and ensure that the edges of flat objects receive treatment.

In operation and use of apparatus 10, container 12 is placed adjacent to a cash register, hotel desk, nursing station or other easily accessible location.

Means 28 for operating light sources or lamps 24, 26 include a conventional lamp ballast 44 electrically connected to lamps 24, 26, a conventional on/off switch 46 and a conventional AC male connector 48 for connecting to a conventional AC supply (not shown). Upon closing of switch 46, lamps 24, 26 are activated to produce UVC radiation. Shielding members 30, 32 prevent ultraviolet light from passing outwardly from container 12 through openings 14, 16, respectively. Lamps 24, 26 can be safely viewed through ultraviolet light filtered openings 37, 39 for enabling visual verification that lamps 24, 26 are operating properly.

An object to be sanitized is then placed through first opening 14 and onto first slide 18. The object then passes under and past shielding member 30 and continues downwardly along first slide 18 beneath first light source or lamp 24.

As the object moves along slide 18 ultraviolet light from lamp 24 is focused onto the object by reflector 34. As the object moves from slide 18, it strikes baffle 22 is flipped over and is redirected onto slide 20 where it passes beneath second light source or lamp 26. Reflector 36 reflects ultraviolet radiation from lamp 26 onto the object as the object passes beneath lamp 26 and downwardly along slide 20. The object then passes beneath and past shielding member 32 and outwardly through second opening 16. The operator may retrieve the object as it exits opening 16, or a container 50 can be used to collect the object and additional objects as they pass through apparatus 10.

As the object passes downwardly along first slide 18, the upper surface of the object is sanitized by ultraviolet lamp 24, and the opposite surface of the object is sanitized as the object slides downwardly along second slide 20 and beneath ultraviolet lamp 26. Edge surfaces of the object are also sanitized by the ultraviolet light from lamps 24, 26 that is reflected from the reflective interior surfaces 12' of container 12.

The invention in its broader aspects is not limited to the specific details shown and described, and departures may be made from such details without departing from the principles of the invention and without sacrificing its chief advantages.

What is claimed is:

1. Apparatus for sanitizing objects by use of ultraviolet light, comprising:

an enclosed container defining a first object entry opening of predetermined height and a second object exit opening of at least said predetermined height;

a first inclined slide mounted within said container and positioned adjacent to and below said first entry opening;

a second inclined slide mounted within said container beneath said first slide and having an end positioned adjacent to and below said second exit opening;

said first and second inclined slides positioned at angles with respect to horizontal such that the pull of gravity on said objects moving down each of said slides is greater than restraining electrostatic and frictional forces on said objects;

a baffle mounted within said container and positioned with respect to said first and second slides for redirecting objects from said first slide onto said second slide;

a first ultraviolet light source mounted within said container and positioned above said first slide;

a second ultraviolet light source mounted within said container and positioned above said second slide; and means in operative relationship with said first and second light sources for selectively operating said light sources.

2. Apparatus as in claim 1 further including:

a first ultraviolet light shielding member yieldingly mounted within said container adjacent to said first entry opening and adjacent to said first slide for enabling said objects to move past said first light shielding member as said objects move downwardly on said first slide; and a second ultraviolet light shielding member yieldingly mounted within said container adjacent to said second exit opening and adjacent to said second slide for enabling said objects to move past said second light shielding member as said objects move downwardly on said second slide to and through said exit opening.

3. Apparatus as in claim 1 further including:

a first ultraviolet light reflector mounted within said container above said first slide and above said first light source; and a second ultraviolet light reflector mounted within said container above said second slide and above said second light source.

4. Apparatus as in claim 3 wherein each of said first and second reflectors defines a parabolic shape and is positioned with said first and second light sources at the focus of said first and second reflectors, respectively.

5. Apparatus as in claim 1 wherein said container further defines first and second ultraviolet light filtered openings positioned adjacent to said first and second ultraviolet light sources, respectively, for enabling visual verification that said first and second light sources are operating properly.

6. Apparatus as in claim 1 wherein said baffle defines a substantially circular arc.

7. Apparatus as in claim 6 for sanitizing said objects up to 2R in length and less than said predetermined height wherein said first slide defines a first end positioned adjacent to and below said first entry opening and a second end positioned adjacent to said baffle and wherein said baffle has a radius of R with a center of said arc positioned substantially directly below said second end at a distance of substantially ⅔ R from said second end and wherein said arc subtends an angle A equal to −2.33B plus 134 where B is the angle of said first slide with respect to horizontal and wherein said arc further extends upwardly beyond an imaginary extension line from said first slide by a perpendicular distance at least equal to the height of said first opening.

8. Apparatus as in claim 7 wherein said baffle is tangentially connected to said second slide.

9. Apparatus as in claim 1 wherein said container defines interior surfaces substantially covered with material for reflecting ultraviolet light from said light sources.

10. Apparatus as in claim 1 wherein said second slide and said baffle are connected together to form a continuous surface for enabling said objects to move from said baffle onto said second slide.

* * * * *